(12) United States Patent
Beaulier et al.

(10) Patent No.: US 10,603,158 B2
(45) Date of Patent: Mar. 31, 2020

(54) METHODS FOR WHIP-STITCHING TISSUE AND TISSUE CONSTRUCTS FORMED THEREBY

(71) Applicants: Smith & Nephew, Inc., Memphis, TN (US); Smith & Nephew Pte. Limited, Singapore (SG); Smith & Nephew Orthopaedics AG, Baar (CH)

(72) Inventors: Duane Beaulier, Memphis, TN (US); Mason Bettenga, Memphis, TN (US); Hadi El Heneidi, Memphis, TN (US); Kangqiao Li, Providence, RI (US); Jennifer Ng, Quincy, MA (US)

(73) Assignees: Smith & Nephew, Inc., Memphis, TN (US); Smith & Nephew Orthopaedics AG (CH); Smith & Nephew Ptd. Limited, Singapore (SG)

(*) Notice: Subject to any disclaimer, the term of this patent is extended or adjusted under 35 U.S.C. 154(b) by 173 days.

(21) Appl. No.: 16/002,430

(22) Filed: Jun. 7, 2018

(65) Prior Publication Data
US 2019/0374330 A1    Dec. 12, 2019

(51) Int. Cl.
*A61F 2/08*    (2006.01)
*A61B 17/06*    (2006.01)
*A61B 17/00*    (2006.01)

(52) U.S. Cl.
CPC ...... *A61F 2/0805* (2013.01); *A61B 17/06066* (2013.01); *A61B 17/06166* (2013.01); *A61B 2017/00969* (2013.01)

(58) Field of Classification Search
CPC .......... A61F 2/08; A61F 2/0805; A61B 17/06; A61B 17/06166; A61B 17/06066; A61L 17/00
See application file for complete search history.

(56) References Cited

U.S. PATENT DOCUMENTS

2001/0051815 A1* 12/2001 Esplin ................ A61B 17/0401
606/232
2012/0253465 A1* 10/2012 Missos ...................... A61F 2/08
623/13.19

* cited by examiner

*Primary Examiner* — Vi X Nguyen
(74) *Attorney, Agent, or Firm* — Burns & Levinson LLP; Joseph M. Maraia; Marlo Schepper Grolnic (57) ABSTRACT

Methods for whip-stitching soft tissue with a needle and a looped suture avoid placing the tissue graft through the suture loop, which also eliminates the need for passing a tissue clamp through the suture loop. The methods described herein can also include combinations of the techniques described.

20 Claims, 6 Drawing Sheets

METHODS FOR WHIP-STITCHING TISSUE AND TISSUE CONSTRUCTS FORMED THEREBY

TECHNICAL FIELD

The present disclosure relates generally to methods of surgical suturing and, more particularly, to methods for whip-stitching soft tissue grafts.

BACKGROUND

Ligaments are frequently damaged (e.g., detached, torn or ruptured) as the result of injury or accident. A damaged ligament can impede proper stability and motion of a joint and cause significant pain. When ligaments are damaged, surgical reconstruction can be necessary, as the ligaments may not regenerate on their own.

A damaged ligament can be replaced or repaired using various procedures, the choice of which can depend on the particular ligament to be restored and the extent of the damage. A common ligament reconstruction procedure involves using an autograft, which is a portion of the patient's own tendon that would replace the damaged natural ligament. The autograft is often a hamstring tendon, though other tendons, such as a patellar tendon, can be used. The ligament graft can also be obtained from a donor, known as an "allograft." Ligament reconstruction procedures typically require preparation of the ligament graft to secure the graft for passing through the repair site and to strengthen the graft prior to fixation. This preparation may involve cleaning and measuring the graft, and then affixing sutures to free ends of the graft to reinforce it. The reinforcement is intended to maintain the structural integrity of the graft and to allow the graft to be properly tensioned when it is inserted into the repair site, such as a tunnel in bone. Sutures are typically affixed to the graft so that free ends of the suture extend from one or both ends of the graft. These free ends are used to secure the graft, either directly or indirectly.

For ligament reconstruction techniques such as Anterior Cruciate Ligament (ACL) and biceps tenodesis procedures, whip-stitching is frequently used for affixing the sutures to the graft. Traditionally, whip-stitching is performed with a single suture and needle, making three to five up-throws and an equal number of down throws, and piercing through the tissue in a staggered fashion while the tissue is held at one end by a tissue clamp. Alternatively, whip-stitching can be performed with a looped suture and needle by placing the tissue through the suture loop, piercing through the tissue, and repeating the steps as described above. However, placing the tissue through the suture loop often requires passing the tissue clamp through the suture loop as well, adding time and difficulty to the surgical procedure.

SUMMARY

Described herein are methods for whip-stitching soft tissue with a needle and a looped suture, and tissue constructs formed thereby. The methods described herein avoid placing the tissue graft through the suture loop, which also eliminates the need for passing the tissue clamp through the suture loop. The methods of this disclosure can thus be performed faster than typical whip-stitching techniques, allowing for a shortened and simplified surgical procedure. The methods described herein can also include combinations of the techniques thus described.

Further examples of the methods of this disclosure may include one or more of the following, in any suitable combination.

Examples of a method of stitching a soft tissue graft of this disclosure include placing a suture loop/needle construct in the vicinity of a graft in which the graft has a proximal end and a distal end. The suture loop/needle construct is passed through or around the graft at a first location such that the graft does not extend through the suture loop to form a first stitch. The suture loop/needle construct is then passed through or around the graft tendon at a second location such that the graft does not extend through the suture loop to form a second stitch. The second location is different from the first location. The above stitching method is then repeated until a stitched portion with a desired stitching length is obtained on the graft. In examples, the graft is a single strand of unfolded tissue.

In further examples of the method, the needle is attached to the suture loop such that the needle does not move relative to the suture loop. The first location is closer to the distal end of the graft than to the proximal end of the graft. In examples, the first location is about 10 mm to about 40 mm from the distal end of the graft. The second location is between the first location and the distal end of the graft. The first stitch is defined by a portion of the suture loop passing around a side edge of the graft from the first location to the second location. The first stitch is defined by a portion of the suture loop looping around the graft at the first location. In examples, at least one of the first stitch and the second stitch is defined by the needle passing through a portion of the suture loop such that a single strand of the suture loop is on both sides of the needle. In other examples, at least one of the first stitch and the second stitch is defined by the needle passing through a portion of the suture loop such that both strands of the suture loop are on both sides of the needle. In examples, at least one of the first stitch and the second stitch is a "throw" stitch or a "tag" stitch.

Yet further examples of the method include securing the proximal end of the graft to a surgical device such that the surgical device does not pass through the suture loop. Other examples include removing the needle from the suture loop. In examples, forming the first stitch is performed in a manner that is different from the manner of forming the second stitch. In examples, the suture is a #2 suture and the suture comprises a biological material. In examples, the graft is an autograft or an allograft. In examples, the needle comprises Nitinol or stainless steel.

Examples of a suture/tissue construct of this disclosure include a suture/tissue construct formed by the methods described above.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "right side" and "left side" herein is intended only to help in the clear description of the present disclosure and are not intended to limit the structure, positioning and/or operation of the tissue, suture or needle in any manner.

Figure 1A:
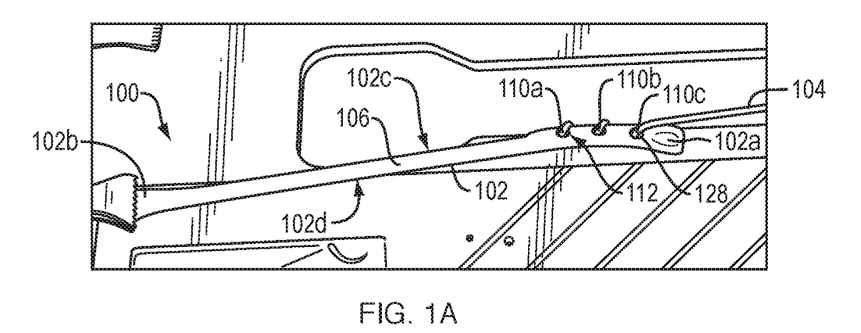
FIG. 1A illustrates a first example of a tissue construct of this disclosure.

Turning now to FIG. 1A, a soft tissue construct 100 formed by an example of the methods of this disclosure is illustrated. As shown in FIG. 1A, the tissue construct 100 includes a graft 102 having first end 102a, a second end 102b, and a suture loop 104. The graft 102 can be a tendon or any other type of autograft or allograft, and can include one or more graft bundles or strands. In examples, the graft 102 is a single strand of non-folded over tissue. The suture loop 104 is passed through a superior surface 106 of the graft 102 at a first origin point 112 that is remote from the first end 102a of the graft 102 such that a terminal length the suture loop 104 remains positioned on the superior surface 106 of the graft 102. The suture loop 104 affixed to the graft 102 has a pattern in the form of a plurality of "luggage tag" or "tag" stitches 110a,b,c that are spaced apart along the length of the graft 102 and that extend from the origin point 112 to a terminal point 128 adjacent to the first end 102a of the graft 102. While three stitches 110a,b,c are shown in FIG. 1A, it should be appreciated that more or fewer than three stitches may be used. Each of the stitches 110a,b,c is defined by a portion of the suture loop 104 passing from the superior surface 106 of the graft 102 at one entry point to the inferior surface (not shown) of the graft 102. Each of the stitches 110a,b passes around the right side edge 102c of the graft 102 to another entry point spaced longitudinally from the origin point 112. In the illustrated example, the stitches 110a,b,c are formed in the direction towards the first end 102a of the graft 102.

The suture loop 104 can be formed from any suitable materials and be of any suitable length. In some examples, the suture can be from size 0 to size 5. In examples, the suture loop 104 is formed from a #2 suture. In some examples, the suture loop 104 can be formed from ultra-high-molecular-weight polyethylene (UHMWPE). In some examples, the suture loop 104 can include High-Molecular Weight-polyethylene (HMWPE) sutures or HMWPE sutures with a co-braid (e.g., monofilament polypropylene, nylon or other co-braid). In some examples, monofilament sutures may be utilized. The suture loop 104 used herein can have any suitable amount and type of bioabsorbable material, which can depend on a particular surgical procedure and/or surgeon preferences. The suture loop 104 may optionally include filaments of various colors.

Figure 1B:
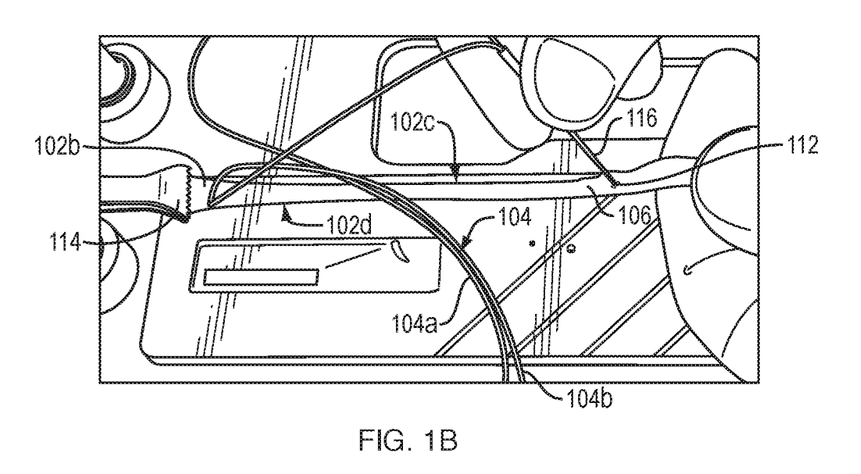
FIGS. 1B-E illustrate a method of forming the tissue construct of FIG. 1A.
Figure 1C:
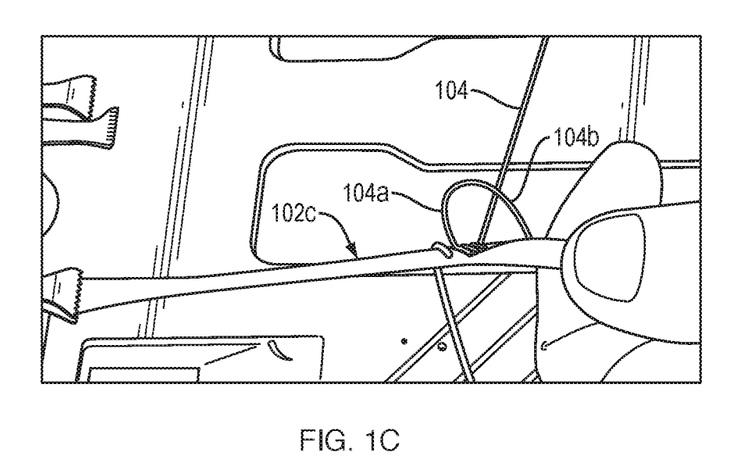

Turning now to FIG. 1B, to form the tissue construct 100 of FIG. 1A, the first and second ends 102a,b of the graft 102 are first secured, for example, by hand or to a tissue clamp 114. A needle 116 is secured to a suture loop 104 (for example, by swaging or crimping) such that the needle 116 does not move relative to the suture loop 104. In examples, the needle 116 is a thin needle comprised of metal (e.g. nitinol or stainless steel) that allows an increased number of stitches through or around the graft 102 with decreased trauma. It should be appreciated that the needle 116 is shown in FIG. 1B for illustration purposes only, as the needle 116 is removed from the tissue construct 100 prior to using the construct 100 in a ligament reconstruction procedure. The needle 116 is then partially advanced through the graft 102 from the superior surface 106 to the inferior surface of the graft 102 at the origin point 112. In examples, the origin point 112 is closer to a midpoint between the right side edge 102c and the left side edge 102d of the graft 102 to avoid tearing at the edges of the graft 102. The origin point 112 is furthermore closer to the first end 102a of the graft 102 than to the second end 102b. In examples, the origin point 112 is about 20 mm from the first end 102a of the graft 102. As shown in FIG. 1C, the needle 116 is then passed through the suture loop 104 near the right side edge 102c of the graft 102 without passing the graft 102 through the suture loop 104. The needle 116 is passed through the suture loop 104 such that first and second strands 104a, 104b of the suture loop 104 are on either side of the needle 116. The suture loop 104 is then cinched, forming the first stitch 110a (FIG. 1D).

Figure 1D:
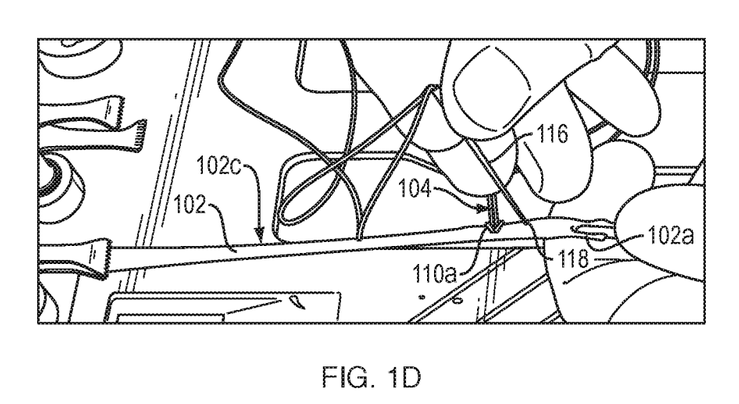
Figure 1E:
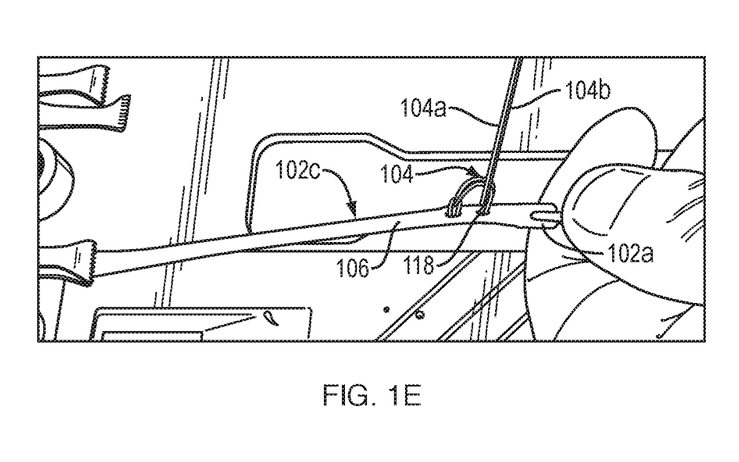

FIG. 1D shows that the first stitch 110a is formed such that the first stitch 110a is disposed around the right side edge 102c of the graft 102. In this way, the stitch 110a locks down on the suture loop 104 positioned at the right side edge 102c of the graft 102. The needle 116 is then moved to the next puncture point 118 on the superior surface 106 towards the first end 102a of the graft 102, causing the suture loop 104 to extend across the superior surface 106 of the graft 102 toward the first end 102a (FIG. 1E). The needle 116 is again partially advanced through the graft 102 from the superior surface 106 to the inferior surface at the puncture point 118. The surgeon then passes his or her fingers through the suture loop 104 on the right side edge 102c of the graft 102. The needle 116 is pulled through the suture loop 104 without pulling the graft 102 through the suture loop 104 such that both of the first and second strands 104a,b are on either side of the needle 116. The suture loop 104 is then cinched to form the second stitch 110b. The steps of FIGS. 1D and 1E are repeated until the desired amount of suture security is achieved on the graft 102. The needle 116 is then removed from the suture loop 104, leaving suture strands 104a,b free to grip during passage and fixation of the graft 102.

It is contemplated by this disclosure that the tissue construct 100 of FIG. 1A could also be formed by rotating the origin point 112 of the needle 116 by 90 degrees (i.e., inferior to superior). It is also contemplated by this disclosure that the stitches could be formed along the left side edge 102d of the graft 102. It should also be appreciated that, although the tissue construct 100 is shown on the first end 102a of the graft 102, a similar tissue construct could be formed on both ends 102a,b of the graft 102. Furthermore, multiple grafts 102 could be used during a surgery, with one or both ends of each of the grafts being prepared as shown in FIGS. 1B-E.

Figure 2A:
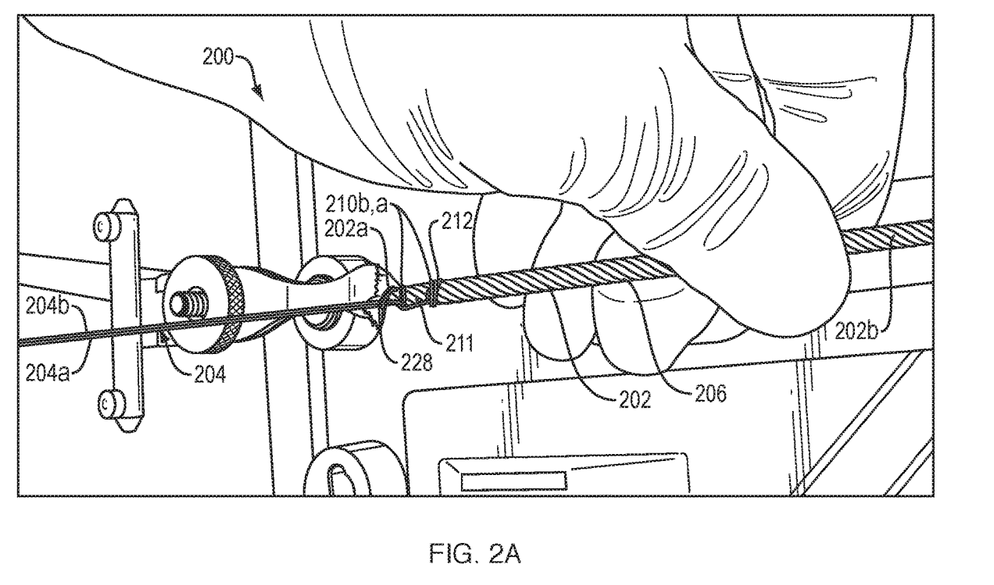
FIG. 2A illustrates a second example of a tissue construct of this disclosure.

Turning now to FIG. 2A, a soft tissue construct 200 formed by another example of the methods of this disclosure is illustrated. As shown in FIG. 2A, the tissue construct 200 includes a graft 202 having a first end 202a, a second end 202b, and a suture loop 204. Both strands 204a,b of the suture loop 204 are looped around the graft 202 at a first origin point 212 that is remote from the first end 202a of the graft 102 such that a terminal length the suture loop 204 remains positioned on the superior surface 206 of the graft 202. The suture loop 204 affixed to the graft 202 has a pattern in the form of a series of "throw" stitches 210a,b and "luggage tag" or "tag" stitches 211 that are spaced apart along the length of the graft 202 and extend from the origin point 212 to a terminal point 228 adjacent to the first end 202a of the graft 202. While two "throw" stitches 210a,b and one "tag" stitch 211 are shown in FIG. 2A, it should be appreciated that any number of "throw" and "tag" stitches may be used. In the illustrated example, the "throw" stitches 210a,b and the "tag" stitch 211 are formed in the direction towards the first end 202a of the graft 202.

Figure 2B:
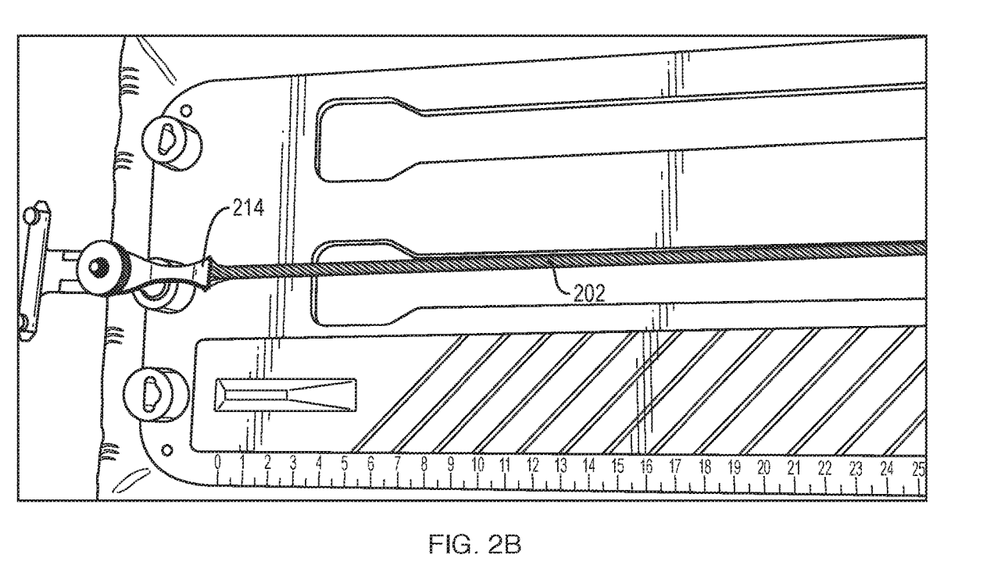
FIGS. 2B-H illustrate a method of forming the tissue construct of FIG. 2A.
Figure 2C:
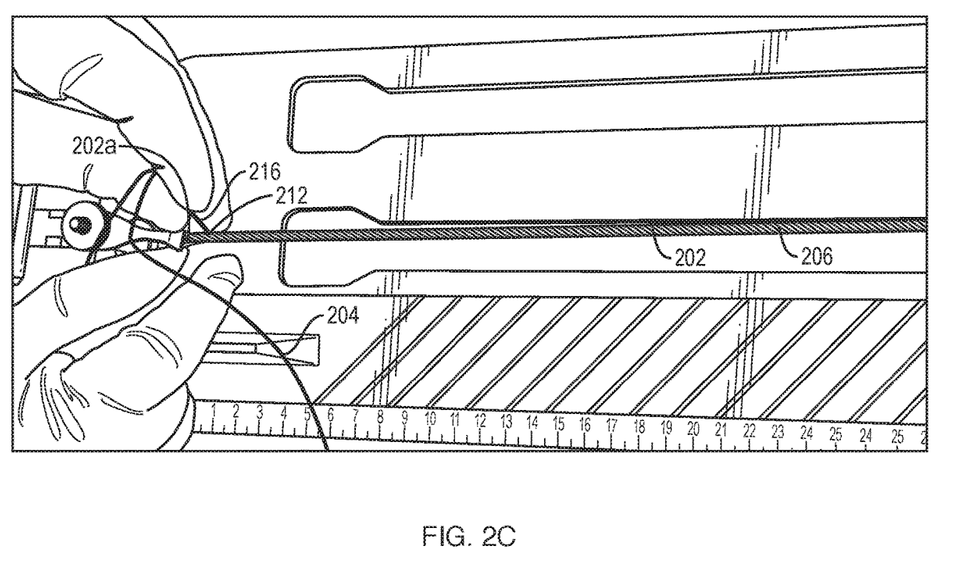
Figure 2D:
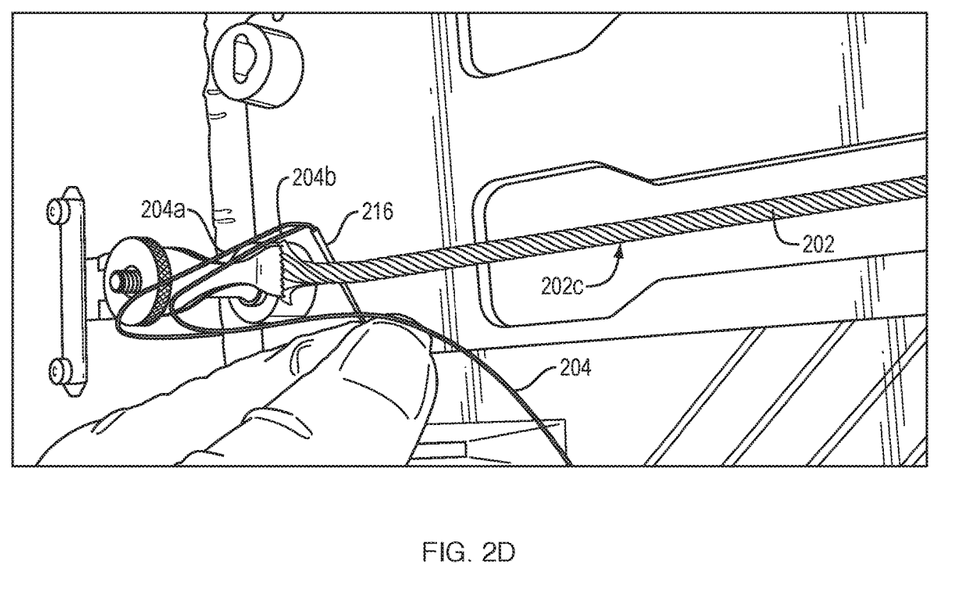
Figure 2E:
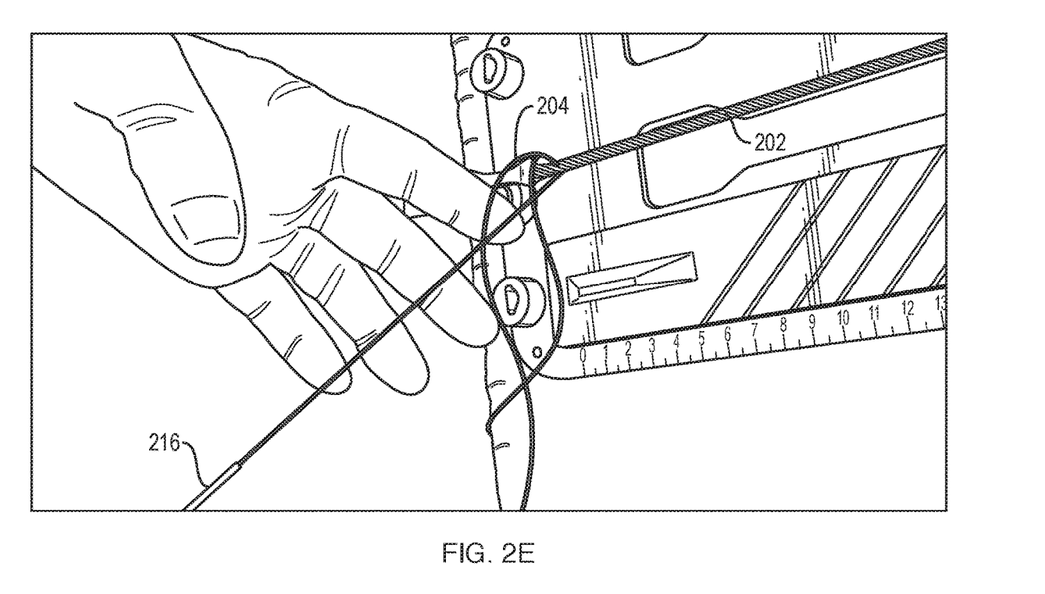

Turning now to FIG. 2B, to form the tissue construct 200 of FIG. 2A, the first end 202a of the graft 202 is first secured (e.g., via tissue clamp 214). As shown in FIG. 2C, a needle 216 is secured to the suture loop 204 such that the needle 216 does not move relative to the suture loop 204. At the origin point 212, which may be spaced between about 10 mm to 40 mm from the first end 202a of the graft 202, the needle 216 is passed from the superior side 206 to the inferior side of the graft 202. As shown in FIG. 2D, the needle 216 is then passed through the suture loop 204 on the right side 202c of the graft 202 without passing the graft 202 through the suture loop 204. Specifically, the needle 216 is passed through the suture loop 204 such that the first and second strands 204a, 204b of the suture loop 204 are on either side of the needle 216. The suture loop 204 is then tightened or cinched by pulling the needle 216 away from the graft 202 (FIG. 2E) to form the first "throw" stitch 210a (FIG. 2F).

Figure 2F:
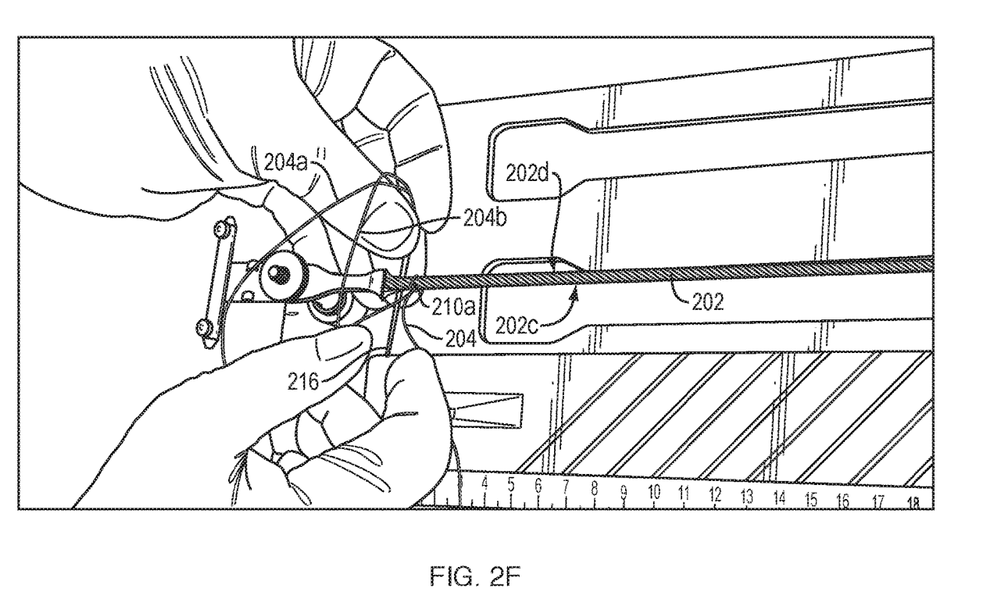
Figure 2G:
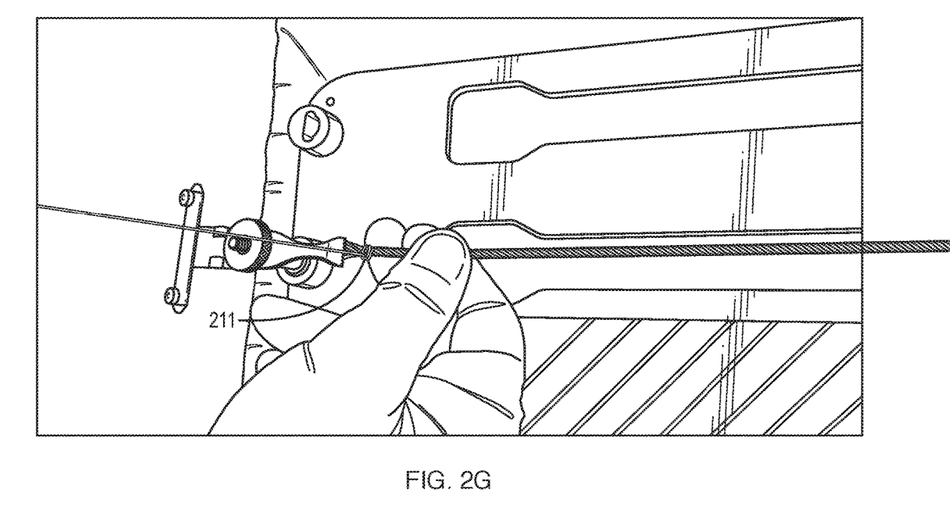
Figure 2H:
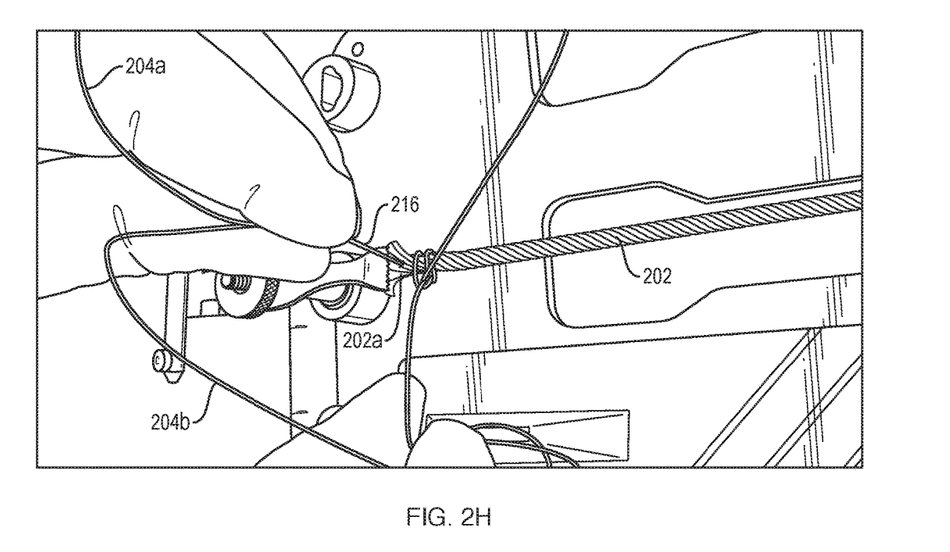

Still referring to FIG. 2F, the needle 216 is moved toward the first end 202a of the graft 202 and passed underneath the graft 202 such that the needle extends from the left side 202d to the right side 202c of the graft 202. The needle 216 is then passed through the suture loop 204 such that the first and second strands 204a, 204b of the suture loop 204 are on either side of the needle 216. The suture loop 204 is then tightened to form the "luggage tag" stitch 211 (FIG. 2G). As shown in FIG. 2H, another "throw" stitch may be formed by first moving the needle closer to the first end 202a and repeating the steps shown in FIGS. 2B-E. The steps for forming the series of "throw" and/or "tag" stitches are repeated until the desired amount of suture security is achieved on the graft 202. The needle 216 is then removed from the suture loop 204, leaving suture strands 204a,b free to grip during passage and fixation of the graft 202.

It is contemplated by this disclosure that a series of "throw" stitches or a series of "tag" stitches could be formed in the graft 202, rather than a "throw-tag-throw" series as shown. It is also contemplated that any combination of "throw" and "tag" stitches could be formed along the graft 202. It should also be appreciated that passing the needle 216 underneath the graft 202 as shown in FIG. 2F could include passing the needle 216 underneath the graft 202 from the right side 202c to the left side 202d, or passing the needle 216 underneath the graft 202 more than once. The origin point 212 of the tissue construct 200 could begin closer or farther than 10 mm to 40 mm from the first end 202a of the graft 202. The needle 216 could be passed from the inferior side of the graft 202 to the superior side 206 of the graft 202 when forming the "throw" or "tag" stitches described above. It should also be appreciated that, although the tissue construct 200 is shown towards the first end 202a of the graft 202 in FIG. 2A, a similar tissue construct could be formed near both ends 202a,b of the graft 202. Furthermore, multiple grafts 202 could be used during a surgery, with one or both ends of each of the grafts being prepared as shown in FIGS. 2B-H.

A person skilled in the art will appreciate that stitches can be formed in other ways different from the manner as shown in FIGS. 1B-E and 2B-H without passing the graft 102,202 through the suture loop 104,204. For instance, the graft can be pieced with the needle from the right side to the left side (or vice versa) of the graft and pulled through to form a stitch across either of the superior or inferior surfaces of the graft. Such stitches could alternately be formed with the "tag" stitches as described above. Alternate examples of tissue constructs could also include combinations of any of the stitches described in this disclosure.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. A method of stitching a soft tissue graft comprising:
   placing a suture loop/needle construct in the vicinity of a graft, the graft having a proximal end and a distal end;
   passing the suture loop/needle construct through or around the graft at a first location such that the graft does not extend through the suture loop to form a first stitch;
   passing the suture loop/needle construct through or around the graft tendon at a second location such that the graft does not extend through the suture loop to form a second stitch, the second location being different from the first location; and
   repeating the above stitching method until a stitched portion with a desired stitching length is obtained on the graft;
   wherein the graft is a single strand of unfolded tissue.

2. The method of claim 1, wherein the needle is attached to the suture loop such that the needle does not move relative to the suture loop.

3. The method of claim 1, wherein the first location is closer to the distal end of the graft than to the proximal end of the graft.

4. The method of claim 1, wherein the first location is about 10 mm to about 40 mm from the distal end of the graft.

5. The method of claim 1, wherein the second location is between the first location and the distal end of the graft.

6. The method of claim 1, wherein the first stitch is defined by a portion of the suture loop passing around a side edge of the graft from the first location to the second location.

7. The method of claim 1, wherein the first stitch is defined by a portion of the suture loop looping around the graft at the first location.

8. The method of claim 1, wherein at least one of the first stitch and the second stitch is defined by the needle passing through a portion of the suture loop such that a single strand of the suture loop is on both sides of the needle.

9. The method of claim 1, wherein at least one of the first stitch and the second stitch is defined by the needle passing through a portion of the suture loop such that both strands of the suture loop are on both sides of the needle.

10. The method of claim 1, wherein at least one of the first stitch and the second stitch is a "throw" stitch.

11. The method of claim 1, wherein at least one of the first stitch and the second stitch is a "tag" stitch.

12. The method of claim 1, further comprising securing the proximal end of the graft to a surgical device, and wherein the surgical device does not pass through the suture loop.

13. The method of claim 1, further comprising removing the needle from the suture loop.

14. The method of claim 1, wherein forming the first stitch is performed in a manner that is different from the manner of forming the second stitch.

15. The method of claim 1, wherein the suture is a #2 suture.

16. The method of claim 1, wherein the suture comprises a biological material.

17. The method of claim 1, wherein the graft is an autograft.

18. The method of claim 1, wherein the graft is an allograft.

19. The method of claim 1, wherein the needle comprises Nitinol or stainless steel.

20. A suture/tissue construct formed by the method of claim 1.

* * * * *